(12) United States Patent
Hoffmann-Emery

(10) Patent No.: US 6,281,353 B1
(45) Date of Patent: Aug. 28, 2001

(54) METHOD OF MAKING DIAZEPINE DERIVATIVES

(75) Inventor: Fabienne Hoffmann-Emery, Birsfelden (CH)

(73) Assignee: Hoffmann-la Roche Inc., Nutley, NJ (US)

( * ) Notice: Subject to any disclaimer, the term of this patent is extended or adjusted under 35 U.S.C. 154(b) by 0 days.

(21) Appl. No.: 09/566,831

(22) Filed: May 8, 2000

(30) Foreign Application Priority Data

May 12, 1999 (EP) .................................................. 99109514

(51) Int. Cl.⁷ ........................ C07D 243/14; C07D 487/04
(52) U.S. Cl. ............................................. 540/496; 540/506
(58) Field of Search ..................................... 540/496, 506

(56) References Cited

U.S. PATENT DOCUMENTS

| | | | |
|---|---|---|---|
| 4,352,815 | 10/1982 | Hunkeler et al. | 424/273 R |
| 4,352,817 | 10/1982 | Hunkeler et al. | 424/273 R |
| 4,352,818 | 10/1982 | Hunkeler et al. | 424/273 R |

FOREIGN PATENT DOCUMENTS

| | | |
|---|---|---|
| 059 386 | 9/1982 | (EP) . |
| 059 389 | 9/1982 | (EP) . |
| 059 390 | 9/1982 | (EP) . |

OTHER PUBLICATIONS

Kamal et al. (Synlett (1999), (8), 1251–1252), 1998.*
Jolivet–Fouchet (Heterocycles (1999), 51(6), 1257–1273.*
Dudasko et al. (Conf. Org. Chem. Adv. Org. Chem., 22nd (1997), 142–143).*
Pfaendler et al. (Heterocycles (1995), 40(2), 717–727).*
Bhat et al. (Tetrahedron (1993), 49(46), 10655–62).*
G.M. Coppola, The Chemistry of Isatoic Anhydride, Synthesis, Georg Thieme Verlag, pp. 505–536 (1980).

* cited by examiner

*Primary Examiner*—Bruck Kifle
(74) *Attorney, Agent, or Firm*—George W. Johnston; William H. Epstein

(57) ABSTRACT

The present invention relates to a process for manufacturing diazepine derivatives of the general formula I

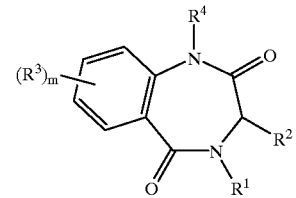

wherein $R^1$ is lower alkyl and $R^2$ is hydrogen, or $R^1$ and $R^2$ are together —$(CH_2)_n$— and n is 2 or 3; $R^3$ is halogen, lower alkyl, lower alkoxy and m is 0, 1 or 2; $R^4$ is hydrogen or lower alkyl.

The compounds of general formula I are valuable intermediate products for the manufacture of imidazo [1,5-a][1,4] diazepine derivatives, like for instance 7-chloro-3-(5-dimethylaminomethyl-[1,2,4]oxadiazol-3-yl)-5-methyl-4,5-dihydro-imidazo[1,5-a][1,4]benzodiazepin-6-one, which diazepine derivatives show excellent psychopharmacological properties as agonists of the central benzodiazepine receptors.

20 Claims, No Drawings

METHOD OF MAKING DIAZEPINE DERIVATIVES

CROSS REFERENCE TO RELATED APPLICATION

The present application is related to copending application Ser. No. 09/566,832 filed on even date herewith, entitled "Imidazodiazepine Derivative," by inventors F. Emery, W. J. Hunkeler, F. Jenck, J. R. Martin and A. Sleight.

BACKGROUND

Conventional means for making intermediate products used in the maufacture of imidazo[1,5-a][1,4]diazepine derivatives have been chracterised by low yields resulting in higher production costs for the final products. The low yields of the conventional production methods have also lead to problems regarding the disposal of unwanted byproducts which are concomitantly produced with the production of the desired intermediates.

SUMMARY OF THE INVENTION

The present invention relates to a process for manufacturing diazepine derivatives of the general formula

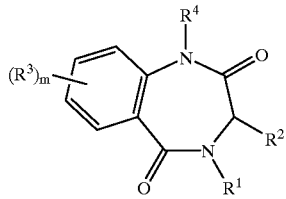

I wherein $R^1$ is lower alkyl;

$R^2$ is hydrogen; or $R^1$ and $R^2$ are together —$(CH_2)_n$— and n is 2 or 3;

$R^3$ is halogen, lower alkyl, lower alkoxy and m is 0, 1 or 2; and $R^4$ is hydrogen or lower alkyl.

The compounds of general formula I are valuable intermediate products for the manufacture of imidazo[1,5-a][1,4]diazepine derivatives, like for instance 7-chloro-3-(5-dimethylaminomethyl-[1,2,4]oxadiazol-3-yl)-5-methyl-4,5-dihydro-imidazo[1,5-a][1,4]benzodiazepin-6-one, which diazepine derivatives show excellent psychopharmacological properties as agonists of the central benzodiazepine receptors.

DETAILED DESCRIPTION OF THE INVENTION

The compounds of general formula I are obtained by the known process consisting of reacting a compound of general formula

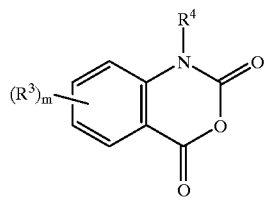

II wherein $R^3$ is halogen, lower alkyl, lower alkoxy and m is 0, 1 or 2; and $R^4$ is hydrogen or lower alkyl.

, with a compound of general formula

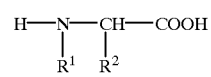

III wherein $R^1$ is lower alkyl;

$R^2$ is hydrogen; or $R^1$ and $R^2$ are together —$(CH_2)_n$— and n is 2 or 3.

This reaction step takes place in a polar solvent such as for instance DMF, under atmospheric pressure and at a temperature between 110° C. and the boiling point of the reaction mixture.

The compounds of formula II can be obtained, on their turn, by reacting a compound of formula

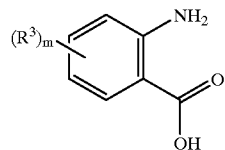

IV wherein $R^3$ is halogen, lower alkyl, lower alkoxy and m is 0, 1 or 2.

, with:

a) phosgene and hydrochloric acid in THF; or b) ethyl haloformiate, e.g. ethyl chloroformate, in dioxane and subsequent treatment with acetylchloride.

Both steps take place in a batch system, under atmospheric pressure and at the boiling temperature of the reaction mixture (see e.g. G. M. Coppola, "The Chemistry of Isatoic Anhydride", *Synthesis*, Georg Thieme Verlag, (1980), pp 505–535).

The last step of the mentioned production pathway is characterised by low yields. This is mainly due to a low conversion of the reactants and, in certain cases, also to a low selectivity towards the desired product because of the formation of a side product of general formula

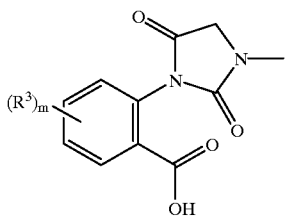

These low yield and selectivity imply higher costs for the production of the compounds of formula I and lead to important disposal problems since the compounds of formula V cannot be used for other purposes and must be therefore destroyed or recycled.

The above elucidated problems are addressed by the present invention by providing a process for manufacturing the compounds of general formula I which can overcome the disadvantages mentioned above.

The problem is solved, according to the present invention, by a process for manufacturing diazepine derivatives of the general formula I, comprising the step of reacting a compound of general formula II with a compound of general formula III, characterised in that said compound of general formula II and said compound of general formula III undergo chemical reaction in the absence of a solvent or in the presence of an apolar solvent.

It has been surprisingly found that the conversion, and in certain cases also the selectivity, towards the compound of formula I strongly increases if the reaction components (i.e. compounds of formula II and III) are not solvated in the reaction mixture. This situation can take place only if no solvent at all is added to the reaction mixture or if the reactants and/or products are not soluble in a given solvent. Being the present compounds of polar nature, apolar solvents can be used in the process of the invention for achieving the wished results.

Particularly preferred solvents are substituted benzene rings, such as xylenes, mesitylene, ethylbenzene, isopropylbenzene, etc. Most preferably, p-xylene or a mixture of xylenes are used as solvent for carrying out the process according to the present invention.

The reaction temperature is preferably set from 0 to 30° C. under the boiling temperature of the reaction mixture.

The process of the present invention is particularly suitable for the manufacture of 6-Chloro-3,4-dihydro-4-methyl-2H-1,4-benzodiazepine-2,5(1H)-dione.

By way of examples, preferred embodiments of the present invention will now be described. Comparative tests were made in which the compounds of formulae II and III underwent reaction in the conventional manner, i.e. using DMF as (polar) solvent.

The yields of compound I (Y(CI)) depicted in Table 1 were measured on the purified product. The ratios of compounds I and V depicted in Table 2 (R(CI) and R(CV)) were directly obtained from the HPLC measurements (HP1050, column CC70/4 nucleosil 100-5Cl8HD), and refer to the molar percentage of CI and CV in the crude product of the reaction.

Y(CI)=100[mol CI/mol CII]

CI, CII, CV=compound of general formula I, II, V

EXAMPLE 1

6-Chloro-3,4-dihydro-4-methyl-2H-1,4-benzodiazepine-2,5(1H)-dione 25.0 g (126 mMol) 5-chloro-1H-benzo[d][1,3]xazin-2,4-dione and 12.4 g (139 mMol) sarcosine were suspended in 100 ml p-xylene and heated at reflux (oil bath temperature ($T_{ext}$) <150° C.) for 2 hours. After cooling to room temperature (r.t.), the suspension was stirred one more hour. The precipitate was filtered off, washed with 25 ml p-xylene twice and dried at 50° C. under vacuum. The solid obtained was digested in 75 ml water one hour at 0° C., filtered off, washed with 25 ml water and dried under vacuum for 18 hours at 80° C. to yield 25.2 g (88% mol) of 6-chloro-3,4-dihydro-4-methyl-2H-1,4-benzodiazepine-2,5(1H)-dione of m.p.=230–232° C.

MS (EI): 224 (M$^{\cdot+}$, 52); 153 (68); 44(100).

EXAMPLE 2

6-Methyl-3,4-dihydro-4-methyl-2H-1,4-benzodiazepine-2,5(1H)-dione 1.0 g (5.6 mMol) 5-methyl-1H-benzo[d][1,3]xazin-2,4-dione and 0.57 g (6.4 mMol) sarcosine were suspended in 4 ml p-xylene and heated at reflux ($T_{ext}$<150° C.) for 5.5 hours. p-Xylene was removed under reduced pressure and the solid residue was digested in 5.0 ml water one hour at 0° C., filtered off, and dried under vacuum for 18 hours at 80° C. to yield 0.93 g (81% mol) of 6-methyl-3,4-dihydro-4-methyl-2H-1,4-benzodiazepine-2,5(1H)-dione of m.p.= 203.5–205° C.

MS (EI): 204 (M$^{\cdot+}$, 94); 175 (38); 133 (100); 44 (100).

EXAMPLE 3

7-Fluoro-3,4-dihydro-4-methyl-2H-1,4-benzodiazepine-2,5(1H)-dione 1.0 g (5.5 mMol) 6-fluoro-1H-benzo[d][1,3]xazin-2,4-dione and 0.54 g (6.1 mMol) sarcosine were suspended in 4.0 ml p-xylene and heated to reflux for 4 hours. The suspension was cooled to r.t. and the precipitate filtered off. The solid obtained was digested 30 minutes at 0° C. in 5 ml deionised water, filtered off and dried for 16 hours at 60° C. under vacuum to yield 0.92 g (80% mol) of 7-fluoro-3,4-dihydro-4-methyl-2H-1,4-benzodiazepine-2,5(1H)-dione of m.p.>250° C.

MS (EI): 208 (M$^{\cdot+}$, 94); 179 (100); 137(92).

EXAMPLE 4

7-Chloro-6-fluoro-3,4-dihydro-4-methyl-2H-1,4-benzodiazepine-2,5(1H)-dione 1.0 g (4.6 mMol) 5-chloro-6-fluoro-1H-benzo[d][1,3]xazin-2,4-dione and 0.45 g (5.0 sarcosine were suspended in 4.0 ml p-xylene and heated to reflux ($T_{ext}$=145° C.) for 7 hours. Solvent was removed under reduced pressure and the residue was digested in 2.0 ml deionised water 1 hour at r.t. The precipitate was filtered off and crystallized from 10 ml methanol and 10 ml diethylether to give 0.63 g (56% mol) of 7-chloro-6-fluoro-3,4-dihydro-4-methyl-2H-1,4-benzodiazepine-2,5(1H)-dione of m.p. >250° C.

Concentration of the mother liquors and crystallization from 3 ml methanol and 9 ml diethylether gave an additional 0.13 g (11%) of 7-chloro-6-fluoro-3,4-dihydro-4-methyl-2H-1,4-benzodiazepine-2,5(1H)-dione of m.p. >250° C.

MS (EI): 242 (M$^{\cdot+}$, 56); 213 (58); 171(76); 44 (100).

EXAMPLE 5

(S)-6-Chloro-1,2,3,11a-tetrahydro-5H-pyrrolo[2,1-c][1,4]-benzodiazepine-5,11(10H)-dione 0.50 g (2.5 mMol) 5-chloro-1H-benzo[d][1,3]xazin-2,4-dione and 0.32 g (2.8 mMol) L-proline were suspended in 4.0 ml p-xylene and heated at reflux ($T_{ext}$<150° C.) for 2.5 hours (gives a yellow solution). Upon cooling to r.t., a precipitate formed which was filtered off and dried at 60° C. under vacuum. The solid obtained was digested in 1.5 ml water one hour at 0° C., filtered off, washed with 1.0 ml water and dried under vacuum for 16 hours at 60° C. to give 0.49 g (78% mol) of (S)-6-chloro-1,2,3,11a-tetrahydro-5H-pyrrolo[2,1-c][1,4]-benzodiazepine-5,11(10H)-dione of m.p. >250° C.

MS (EI): 250 ($M^{\cdot+}$, 40); 221 (30); 70(100).

EXAMPLE 6

(S)-1,10a-5-Chloro-2H-azeto[2,1-c][1,4] benzodiazepine-4,10(9H)-dione 1.0 g (5.1 mMol) 5-chloro-1H-benzo[d][1,3]xazin-2,4-dione and 0.56 g (5.6 mMol) (S)-azetidine-2-carboxylic acid were suspended in 6.0 ml p-xylene and heated to reflux for 24 hours. p-Xylene was removed under reduced pressure and the residue was partitioned between dichloromethane and water and the aqueous phase extracted with dichloromethane. The combined organic extracts were dried ($Na_2SO_4$) and the solvent removed under reduced pressure. The brown solid obtained was digested in 5 ml tert-butyl-methylether for 16 hours at r.t., filtered and dried under reduced pressure to give 0.99 g (82% mol) of (S)-1,10a-5-chloro-2H-azeto[2,1-c][1,4]benzodiazepine-4,10(9H)-dione as a beige powder of m.p.=180–198° C.

MS (EI): 236 ($M^{\cdot+}$, 44); 180 (24); 153(62), 56 (100).

EXAMPLE 7

(S)-1-Methyl-1,2,3,11a-tetrahydro-5H-pyrrolo[2,1-c][1,4]-benzodiazepine-5,11(10H)-dione 0.5 g (2.82 mMol) N-metyl-1H-benzo[d][1,3]xazin-2,4-dione and 0.36 g (3.1 mMol) L-proline were suspended in 1.0 ml p-xylene and heated to reflux for 1 hour (goes into solution upon heating). After cooling to r.t., the reaction mixture was diluted with 10 ml dichloromethane and 5 ml deionised water and the phases separated. The aqueous phase was extracted with 8 ml dichloromethane twice. The combined organic extracts were dried ($Na_2SO_4$) and evaporated. The residue was digested in 2 ml tert-butyl-methylether for 2 hours at r.t. to give 0.53 g (81.5% mol) of (S)-1-methyl-1,2,3,11a-tetrahydro-5H-pyrrolo[2,1-c][1,4]-benzodiazepine-5,11(10H)-dione as beige crystals of m.p.=117–118.5° C.

MS (EI): 230 ($M^{\cdot+}$, 56); 161 (99); 133 (90); 105 (88); 70(100).

EXAMPLE 8

6-Chloro-3,4-dihydro-4-methyl-2H-1,4-benzodiazepine-2,5(1H)-dione 1.0 g (5.0 mMol) 5-chloro-1H-benzo[d][1,3]xazin-2,4-dione and 0.50 g (5.56 mMol) sarcosine were suspended in 4.0 ml of a mixture of xylenes and heated at reflux ($T_{ext}$<150° C.) for 4 hours. After cooling to room temperature, the suspension was stirred one more hour. The precipitate was filtered off, washed with 1.5 ml hexane twice and dried at 60° C. under vacuum. The solid obtained was digested in 3.0 ml water one hour at 0° C., filtered off, washed with 2.0 ml water and dried under vacuum for 4 hours at 60° C. to yield 0.86 g (74% mol) of 6-chloro-3,4-dihydro-4-methyl-2H-1,4-benzodiazepine-2,5(1H)-dione of m.p.=235–237° C.

MS (EI): 224 ($M^{\cdot+}$, 48); 195(34); 153(60) 126(36), 44(100).

EXAMPLE 9

7-Chloro-3,4-dihydro-4-methyl-2H-1,4-benzodiazepine-2,5(1H)-dione 1.0 g (5.06 mMol) 6-chloro-1H-benzo[d][1,3]xazin-2,4-dione and 0.67 g (7.59 mMol) sarcosine were thoroughly mixed and heated to 140° C. for 2 hours then 150° C. for 20 hours. The brown powder obtained was cooled to r.t. and digested in 4.0 ml water at 0° C. for 1 hour, filtered and washed with 1.0 ml water. After drying under vacuum, 1.0 g (88% mol) 7-chloro-3,4-dihydro-4-methyl-2H-1,4-benzodiazepine-2,5(1H)-dione was obtained as a beige powder of m.p. >250° C.

MS (EI): 224 ($M^{\cdot+}$, 78); 195(86); 153(80), 44(100).

EXAMPLE 10

(S)-6-Chloro-1,2,3,11a-tetrahydro-5H-pyrrolo[2,1-c][1,4]-benzodiazepine-5,11(10H)-dione 0.50 g (2.5 mMol) 5-chloro-1H-benzo[d][1,3]xazin-2,4-dione and 0.43 g (3.75 mMol) L-proline were finely ground together and heated to 150° C. for 18 hours. The brown powder obtained was digested in 2.0 ml water at 0° C. for 1 hour, filtered off and washed with 2.0 ml cold water to yield, after drying under vacuum, 0.57 g (91% mol) (S)-6-chloro-1,2,3,11a-tetrahydro-5H-pyrrolo[2,1-c][1,4]-benzodiazepine-5,11(10H)-dione as a beige powder of m.p. >250° C.

MS (EI): 250 ($M^{\cdot+}$, 36); 221 (28); 194(28); 153(32); 126(30); 70(100).

TABLE 1

Reaction yields after purification.

| Ex. No | Process of the invention Y(CI) | Comparative examples Y(CI) |
|---|---|---|
| 1 | 88.0 | 65.0 |
| 2 | 81.0 | 58.0 |
| 3 | 80.0 | 74.5 |
| 4 | 67.0 | 40.0 |
| 5 | 78.0 | 71.0 |
| 6 | 82.0 | 10.0 |
| 7 | 81.5 | not measured |
| 8 | 74.0 | 65.0 |
| 9 | 88.0 | 69.0 |
| 10 | 91.0 | 71.0 |

TABLE 2

Ratios of CI and CV in the crude product

| | Process of the invention | | Comparative examples | |
|---|---|---|---|---|
| Ex. No | R(CI) | R(CV) | R(CI) | R(CV) |
| 1 | 96.7 | 2.7 | 76.0 | 20.0 |
| 3 | 97.7 | — | 86.0 | 12.0 |

As showed in the above tables, the process according to the present invention leads to yields in the desired product which are much higher than those obtainable with conventional processes. Therefore, the process according to the present invention enables a surprising increase of the productivity, thereby decreasing costs and disposal problems.

As stated above, the products obtained with the process according to the invention can be used for manufacturing imidazo [1,5-a][1,4]diazepine derivatives with excellent psychoarmacological properties. Example 11 illustrates a possible method for producing one of such diazepine derivatives.

EXAMPLE 11

7-Chloro-3-(5-dimethylaminomethyl-[1,2,4] oxadiazol-3-yl)-5-methyl-4,5-dihydroimidazo[1,5-a][1,4]benzodiazepin-6-one Ethyl 7-chloro-5,6-dihydro-5-methyl-6-oxo-4H-imidazo[1,5-a][1,4]benzodiazepine-3-carboxylate 25.0 g 6-Chloro-3,4-dihydro-4-methyl-2H-1,4-benzodiazepine-2,5(1H)-dione were suspended under stirring and argon atmosphere in 200 ml toluene and 32.1 ml N,N-dimethyl-p-toluidine. The suspension was heated to 100° C. and 11.2 ml phosphorus oxychloride were added over 30 minutes and stirring was pursued two and an half hours at 100° C. The dark-orange solution was cooled to 40° C. and toluene was removed under reduced pressure to give 82 g of a dark-orange oil.

Meanwhile, 81.2 ml hexamethyldisilazane and 265 ml tetrahydrofuran were mixed and cooled to −35° C. 229.5 ml Butyllithium were added over 45 minutes and, after stirring 30 minutes at −35° C., a solution of 35.2 g ethyl (dimethylamino-methylenamino)acetate in 70.4 ml tetrahydrofuran was added over 30 minutes. The orange solution obtained was stirred one more hour at −35° C. and a solution of the crude iminochloride in 100 ml tetrahydrofuran was added over 1 hour at −15° C. The dark red solution was stirred one hour at −15° C., then 18 hours at room temperature (r.t.). 75 ml Acetic acid were added in 10 minutes, then 75 ml deionized water were added in one portion and the orange suspension was heated at reflux for two hours. Tetrahydrofuran was removed under reduced pressure and the residue was partitioned between 200 ml dichloromethane and 100 ml deionized water. The phases were separated and the organic phase was washed with 100 ml aqueous HCl 1N twice and with 100 ml deionized water. The aqueous phases were extracted twice with 100 ml dichloromethane. The combined organic extracts were dried (Na$_2$SO$_4$) and evaporated. The residue was digested in 200 ml n-heptane 30 minutes at r.t. and filtered off. The sticky crystals obtained were digested at reflux for 30 minutes in 213.5 ml ethanol, then stirred 3 hours to r.t. and 2 hours at −20° C. The precipitate (ethyl 7-chloro-5,6-dihydro-5-methyl-6-oxo-4H-imidazo[1,5-a][1,4]benzodiazepine-3-carboxylate) was filtered off, washed three times with 20 ml ethanol and dried under reduced pressure 16 hours at 60° C. Crude product: 23.4 g as a beige powder. m.p. 225.5–226.5° C.

7-Chloro-5,6-dihydro-5-methyl-6-oxo-4H-imidazo[1,5-a][1,4]benzodiazepine-3-carboxamide.

22.8 g Ethyl 7-chloro-5,6-dihydro-5-methyl-6-oxo-4H-imidazo[1,5-a][1,4]-benzodiazepine-3-carboxylate were suspended under stirring and argon atmosphere in 91.2 ml 1,4-dioxane. 14.1 ml Formamide and 13.9 ml sodium methanolate were successively added to yield a clear light-orange solution, which turned to a white suspension after 10 minutes. This suspension was stirred two hours at 30° C. 200 ml Deionized water were added in one portion and 1,4-dioxane was distilled off at 40° C. under reduced pressure. The remaining white suspension was stirred two hours at 0° C. and filtered. The precipitate (7-chloro-5,6-dihydro-5-methyl-6-oxo-4H-imidazo[1,5-a][1,4]benzodiazepine-3-carboxamide) was washed with 50 ml deionized water three times and dried under reduced pressure for 18 hours at 80° C. Crude product:19.43 g as a white powder. m.p. >250° C.

7-Chloro-5,6-dihydro-5-methyl-6-oxo-4H-imidazo[1,5-a][1,4]benzodiazepine-3-carbonitrile.

19.0 g 7-Chloro-5,6-dihydro-5-methyl-6-oxo-4H-imidazo[1,5-a][1,4]benzodiazepine-3-carboxamide were suspended under stirring and argon atmosphere in 95 ml 1,4-dioxane and 6.58 ml phosphorous oxychloride were added in one portion. The reaction mixture was heated to reflux for one hour giving a yellow solution, which was concentrated at 50° C. under reduced pressure. The residue was digested in 100 ml deionized water for two hours at r.t. The precipitate (7-chloro-5,6-dihydro-5-methyl-6-oxo-4H-imidazo[1,5-a][1,4]benzodiazepine-3-carbonitrile) was filtered off, washed three times with 30 ml deionized water and dried under vacuum at 80° C. for 18 hours. Crude product: 17.3 g as a light yellow powder. m.p. 238.5–239.5° C.

7-Chloro-5,6-dihydro-5-methyl-6-oxo-4H-imidazo[1,5-a][1,4]benzodiazepine-3-carboxamidoxime.

16.8 g 7-Chloro-5,6-dihydro-5-methyl-6-oxo-4H-imidazo[1,5-a][1,4]benzodiazepine-3-carbonitrile were suspended under stirring and argon atmosphere in 101 ml N,N-dimethylformamide and 13.48 g hydroxylamine hydrochloride were added in one portion. 34.2 ml Sodium methanolate were then added over 60 minutes to the yellow suspension, which turned to a colorless suspension. It was stirred one more hour at r.t., then cooled to 0–2° C. and 202 ml deionized water were added over 30 minutes. After stirring one more hour at 0° C., the precipitate (7-chloro-5,6-dihydro-5-methyl-6-oxo-4H-imidazo[1,5-a][1,4]benzodiazepine-3-carboxamidoxime (VIII)) was filtered off, washed twice with 40 ml deionized water and dried under vacuum at 70° C. for 18 hours. Crude product: 17.84 g as a white powder. m.p. >250° C.

7-Chloro-3-(5-chloromethyl-[1,2,4]oxadiazol-3-yl)-5-methyl-4,5-dihydro-imidazo[1,5-a][1,4]benzodiazepin-6-one.

8.0 g 7-Chloro-5,6-dihydro-5-methyl-6-oxo-4H-imidazo[1,5-a][1,4]benzodiazepine-3-carboxamidoxime and 1.0 g magnesium oxide were suspended under stirring and argon atmosphere in 160 ml 1,4-dioxane. 2.7 ml Chloracetyl chloride were added in one portion and the white thick gel obtained was stirred 4 hours at r.t. and then 17 hours at reflux to give a lightly orange fluid suspension. 100 ml Dioxane were distilled off and the reaction mixture was cooled to room temperature. 180 ml Deionized water were added within 15 minutes and the suspension was stirred 1 hour at r.t. The precipitate was filtered off, washed with 50 ml deionized water twice and dried under vacuum at 80° C. for 18 hours. Crude product: 8.3 g as a light pink powder. This crude product was dissolved in 120 ml tetrahydrofuran at reflux and 0.83 g active charcoal Darco G 60 were added. The system was refluxed 1 hour, then filtered on 25 g Dicalit-Speedex and the filter cake was washed with three portions of 50 ml warm tetrahydrofuran. The filtrate was concentrated at 40° C. under reduced pressure. The residue was digested in 80 ml ethanol 1 hour at reflux, then stirred 16 hours at r.t. and finally 2 hours at 2° C. The precipitate (7-chloro-3-(5-chloromethyl-[1,2,4]oxadiazol-3-yl)-5-methyl-4,5-dihydro-imidazo [1,5-a][1,4]benzo-diazepin-6-one (IX)) was filtered off, washed with 2 portions of 25 ml cold tert-butyl methyl-ether and dried under vacuum 5 hours at 80° C. Crude product: 7.6 g as a light beige powder. m.p. 234–238° C.

7-Chloro-3-(5-dimethylaminomethyl-[1,2,4]oxadiazol-3-yl)-5-methyl-4,5-dihydro-imidazo[1,5-a][1,4]benzodiazepin-6-one. 7.0 g 7-Chloro-3-(5-chloromethyl-[1,2,4]oxadiazol-3-yl)-5-methyl-4,5-dihydro-imidazo-[1,5-a][1,4]benzodiazepin-6-one were suspended under stirring and argon atmosphere in 70 ml 1,4-dioxane and 25.7 ml dimethylamine (33% in ethanol) were added over 60 minutes. The reaction mixture was stirred one more hour at r.t.

and then the solvents were removed under reduced pressure at 35° C. The residue was partitioned between 50 ml dichloromethane and 20 ml deionized water. The phases were separated and the organic phase was washed twice with 20 ml deionized water. The aqueous phases were extracted separately with the same portion of 25 ml dichloromethane, twice. The combined organic extracts were dried (Na$_2$SO$_4$) and the solvent was removed under reduced pressure. Crude product: 8.0 g as a light yellow foam.

Purification

The crude product was dissolved in 40 ml ethanol at reflux and 400 mg active charcoal Darco G 60 were added. The system was stirred 1 hour at reflux, then filtered on a hot pad of Dicalit Speedex, which was washed with two portions of 40 ml hot ethanol. The filtrate was concentrated to 14 g under reduced pressure, heated to reflux and at this temperature and 40 ml tert-butyl-methylether were added over 5 minutes. The suspension was cooled slowly to r.t., stirred 16 hours, further cooled to 2° C. After stirring 1 hour at 2° C., the precipitate was filtered off, washed with 20 ml tert-butyl-methylether and dried 1 hour at 60° C. under vacuum. The so obtained powder was dissolved at reflux in 26 ml ethyl acetate. 6.5 ml Ethyl acetate were then distilled off and the turbid solution obtained was slowly cooled to r.t., then to 0° C. After 1 hour stirring at 0° C., the precipitate was filtered off, washed with 10 ml cold tert-butyl-methylether and dried under vacuum at 60° C. for 16 hours. The so obtained powder (7-chloro-3-(5-dimethylaminomethyl-[1,2,4]oxadiazol-3-yl)-5-methyl-4,5-dihydro-imidazo[1,5-a][1,4]benzodiazepin-6-one (I)) was crystallized a second time in 24.3 ml ethyl acetate according to the procedure described above. Product: 5.5 g as a white powder. m.p. 151.5–153° C.

What is claimed is:

1. A process for manufacturing a compound of formula I

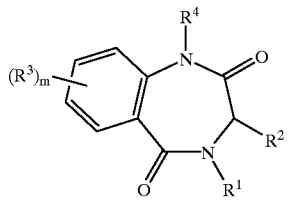

wherein:
$R^1$ is lower alkyl;
$R^2$ is hydrogen;, or
$R^1$ and $R^2$ are together —(CH$_2$)$_n$— and n is 2 or 3;
$R^3$ is halogen, lower alkyl, lower alkoxy and m is 0, 1 or 2; and
$R^4$ is hydrogen or lower alkyl:

comprising, reacting a compound of formula II

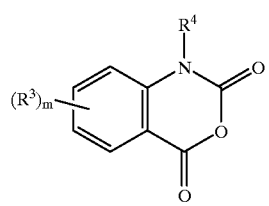

with a compound of formula III

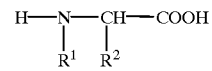

wherein $R^1$, $R^2$, $R^3$, $R^4$, m and n have the meanings set forth above, and said reaction between said compound of formula II and said compound of formula III takes place in the presence of an apolar solvent.

2. The process of claim 1 wherein said reaction takes place in the presence of an apolar solvent.

3. The process according to claim 2, wherein the apolar solvent is a substituted benzene ring.

4. The process according to claim 3, wherein the apolar solvent is p-xylene.

5. The process according to claim 3, wherein the apolar solvent is a mixture of xylenes.

6. The process according to claim 1, wherein the compound of formula I is 6-Chloro-3,4-dihydro-4-methyl-2H-1,4-benzodiazepine-2,5(1H)-dione.

7. The process according to claim 2, wherein the compound of formula I is 6-Chloro-3,4-dihydro-4-methyl-2H-1,4-benzodiazepine-2,5(1H)-dione.

8. The process according to claim 3, wherein the compound of formula I is 6-Chloro-3,4-dihydro-4-methyl-2H-1,4-benzodiazepine-2,5(1H)-dione.

9. The process according to claim 4, wherein the compound of formula I is 6-Chloro-3,4-dihydro-4-methyl-2H-1,4-benzodiazepine-2,5(1H)-dione.

10. The process according to claim 5, wherein the compound of formula I is 6-Chloro-3,4-dihydro-4-methyl-2H-1,4-benzodiazepine-2,5(1H)-dione.

11. The process according to claim 1, wherein the reaction temperature is from 0 to 30° C. under the boiling temperature of the reaction mixture.

12. The process according to claim 2, wherein the reaction temperature is from 0 to 30° C. under the boiling temperature of the reaction mixture.

13. The process according to claim 3, wherein the reaction temperature is from 0 to 30° C. under the boiling temperature of the reaction mixture.

14. The process according to claim 4, wherein the reaction temperature is from 0 to 30° C. under the boiling temperature of the reaction mixture.

15. The process according to claim 5, wherein the reaction temperature is from 0 to 30° C. under the boiling temperature of the reaction mixture.

16. The process according to claim 6, wherein the reaction temperature is from 0 to 30° C. under the boiling temperature of the reaction mixture.

17. The process according to claim 7, wherein the reaction temperature is from 0 to 30° C. under the boiling temperature of the reaction mixture.

18. The process according to claim 8, wherein the reaction temperature is from 0 to 30° C. under the boiling temperature of the reaction mixture.

19. The process according to claim 9, wherein the reaction temperature is from 0 to 30° C. under the boiling temperature of the reaction mixture.

20. The process according to claim 10, wherein the reaction temperature is from 0 to 30° C. under the boiling temperature of the reaction mixture.

* * * * *